United States Patent
Franks et al.

(10) Patent No.: US 6,562,855 B1
(45) Date of Patent: May 13, 2003

(54) ANAESTHETIC FORMULATION COMPRISING AN NMDA-ANTAGOINST AND AN ALPHA-2 ADRENERGIC AGONIST

(76) Inventors: Nicholas Peter Franks, Biophysics Section, Blackett Laboratory, Imperial College of Science, Technology and Medicine, Prince Consort Road, London SW7 2BZ (GB); Mervyn Maze, Sir Ivan Magill Anaesthetics Department, Imperial College School of Medicine, Chelsea and Westminster Hospital, 369 Fullham Road, London SW10 9NH (GB)

( * ) Notice: Subject to any disclaimer, the term of this patent is extended or adjusted under 35 U.S.C. 154(b) by 0 days.

(21) Appl. No.: 10/018,007

(22) PCT Filed: Jun. 9, 2000

(86) PCT No.: PCT/GB00/02271

§ 371 (c)(1),
(2), (4) Date: Dec. 11, 2001

(87) PCT Pub. No.: WO00/76545

PCT Pub. Date: Dec. 21, 2000

(30) Foreign Application Priority Data

Jun. 11, 1999 (GB) .............................................. 9913677

(51) Int. Cl.[7] .......................... A61K 3/415; A61K 9/02
(52) U.S. Cl. ...................... 514/399; 514/816; 514/817; 514/818; 424/40
(58) Field of Search ................................ 514/315, 816, 514/817, 818, 399; 624/40

(56) References Cited

U.S. PATENT DOCUMENTS

| 5,605,911 A | * | 2/1997 | Olney et al. ................. | 514/315 |
| 6,197,323 B1 | | 3/2001 | Georgieff | |
| 6,274,633 B1 | * | 8/2001 | Franks et al. ............... | 514/769 |

FOREIGN PATENT DOCUMENTS

| EP | 0 861 329 A1 | | 9/1998 |
| WO | WO 98/40083 | | 9/1998 |
| WO | WO 00/38678 | | 7/2000 |
| WO | WO2000038678 | * | 7/2000 |
| WO | WO 00/53192 | | 9/2000 |

OTHER PUBLICATIONS

De sousa et al., Contrasting synaptic actions of the inhalational general . . . , Database CAplus, AN 2000:283179, abstract, Anesthesuology, 2000, vol. 92(4), pp. 1055–1066.*
Harris, Adron R., Do intravenous and inhalation anesthetics . . . , Database CAplus AN 1998:799415, abstract, International Congress Series, 1998, vol. 1164(New England Anesthesia), pp. 11–18.*
Beekers, J.M., and Stevens, C.F., Proc. Natl. Acad. Sci. USA 88: 7834–7838, 1988.
Brockmeyer, D.M., and Kendig, J.J., Br. J. Anaesthesia 74: 79–84 (1995).
Cullen, S.C., et al., Anesthesiology 31: 305–309 (1969).
Cullen, S.C., and Gross, E.G., Science 113: 580–582 (1951).
Davies, J., et al., Neurosci. Lett. 21: 77–81 (1981).
Franks, N.P., et al., Nature 396: 324 (1998).
Franks, N.P., and Lieb, W.R., Br. J. Anaesthesia 71: 65–76 (1993).
Franks, N.P., and Lieb, W.R., Nature 367: 607–614 (1994).
Franks, N.P., and Lieb, W.R., Anesthesiology 84: 716–720 (1996).
Goto, T., et al., Anesthesiology 86: 1273–1278 (1997).
Hadingham, K.L., et al., Proc. Natl. Acad. Sci. USA 89: 6378–6382 (1992).
Kennedy, R.R., et al., Anaesth. Intens. Care 20: 66–70 (1992).
Koblin, D.D., et al., Anesth. Anal. 87: 419–424 (1998).
Lachmann, B., et al., Lancet 335: 1413–1415 (1990).
Lawrence, J.H., et al., J. Physiol. 105: 197–204 (1946).
Luttropp, H.H., et al., Acta Anaesthesiol. Scand. 38: 121–125 (1994).
Mennerick, S., et al., J. Neurophysiology 73: 320–332 (1995).
Mihic, S.J., et al. Nature 389: 385–389 (1997).
Sagratella, S., Pharmacological Research 32: 1–13 (1995).
Segal, M.M., and Furshpan, E.J., J. Neurophysiology 64: 1390–1399 (1990).
Smith, R.A., et al., Biochim. Biophys. Acta 645: 327–338 (1981).
Tanelian, D.L., et al., Anesthesiology 78: 757–776 (1993).
Watkins, J.C., and Evans, R.H., Ann. Rev. Pharmacol. Toxicol. 21: 165–204 (1981).
Weathersby, P.K., and Homer, L.D., Undersea Biomedical Res. 7: 277–296 (1980).
Whitehurst, S.L., J. Neurosurgical Anesthesiology 6: 275–279 (1994).
Wlaz, P., et al., Eur. J. Neuroscience 6: 1710–1719 (1994).
Proctor, L.T., et al., Anesthesiology 77: 554–562 (1992).
Sakaguchi, M. et al., Am. J. Vet. Res. 57: 529–534 (1996).

* cited by examiner

Primary Examiner—Phyllis G. Spivack
Assistant Examiner—Vickie Kim
(74) Attorney, Agent, or Firm—St. Onge Steward Johnston & Reens LLC (57) ABSTRACT

A pharmaceutical composition is described. The composition comprises a formulation. The formulation comprises an NMDA antagonist and an alpha-2 adrenergic agonist. In a preferred aspect, there is provided an improved anaesthetic comprising an NMDA antagonist and an alpha-2 adrenergic agonist.

6 Claims, 6 Drawing Sheets

ANAESTHETIC FORMULATION COMPRISING AN NMDA-ANTAGOINST AND AN ALPHA-2 ADRENERGIC AGONIST

CROSS-REFERENCES TO RELATED APPLICATIONS

This application claims priority benefit of PCT/GB00/02271, filed internationally on Jun. 9, 2000, which designated the United States and claimed priority benefit of GB 9913677.2, filed Jun. 11, 1999.

BACKGROUND

The present invention relates to a novel formulation that is capable of displaying one or more beneficial therapeutic effects. By way of example, the novel formulation can provide any one or more of general anaesthesia, analgesia, conscious sedation and neuroprotection.

The state of general anaesthesia encompasses several elements, namely, analgesia (or insensibility to a noxious stimulus), loss of consciousness (hypnotic response), attenuation of the sympathetic nervous system responses to a noxious stimulus (sympatholysis), interruption of memory formation of untoward events, and muscle relaxation.

The state of general anaesthesia is usually produced by a combination of several drugs from different pharmacological classes, as to date no class of compound alone provides the ideal features which are required. For example, potent volatile anaesthetic agents such as halogenated ethers and haloalkanes, may be biotransformed to potentially toxic agents. Also these agents cause excitation on emergence from anaesthesia. Inhalation agents such as nitrous oxide and xenon are not considered to be potent enough to be used as monotherapy, whereas sedative/hypnotic agents (including propofol, benzodiazepines and barbiturates) lack analgesic properties. Analgesics either produce severe respiratory depression requiring assisted ventilation (in the case of the opioids) or do not produce a hypnotic response (non-opioids), whereas peripherally-acting muscle relaxants (e.g., vecuronium and atracurium) have neither analgesic or hypnotic properties.

In view of the prior art, it is clear that there are a number of drawbacks associated with the drugs currently used for general anaesthesia. Firstly, there is a need for specialised drug delivery systems, particularly for potent volatile anaesthetics. This need is obviated by using the intravenous route (total intravenous anaesthesia, otherwise known as "TIVA"). However, current TIVA regimens invariably include analgesic agents (e.g. opiate narcotics) which cause respiratory depression and hypnotic agents (propofol and barbiturates) which cause cardiac depression, thus requiring equipment for ventilatory and cardiovascular support during its use. Secondly, termination of the clinical effect from TIVA requires either biotransformation and/or elimination of the parent drug and their metabolites which may lead to organ toxicity problems. Other disadvantages of these drugs include prolonged emergence associated with excitation, nausea and vomiting (all except propofol), high addictive potential, together with a narrow window of therapeutic efficacy. Finally, there is also the environmental threat associated with the destruction of the ozone layer by nitrous oxide.

The present invention seeks to provide an improved formulation for general pharmaceutical use, especially for use in anaesthesia.

STATEMENT OF INVENTION

Aspects of the present invention are presented in the accompanying claims and in the following description.

DETAILED DESCRIPTION

In a broad aspect, the present invention provides a pharmaceutical comprising an NMDA antagonist and an alpha-2 adrenergic agonist.

In a preferred embodiment, the present invention provides an anaesthetic comprising an NMDA antagonist and an alpha-2 adrenergic agonist.

Surprisingly, we have found that the co-administration of an NMDA receptor antagonist and an alpha-2 adrenergic agonist, preferably as a single formulation, both enhances the efficacy of the individual compounds through a synergistic mechanism, but also diminishes the likelihood of the adverse and unwanted side effects that these drugs can cause when used alone.

One essential component of the formulation is an NMDA receptor antagonist.

The term "anatagonist" is used in its normal sense in the art, i.e., a chemical compound which prevents functional activation of a receptor by its agonist (NMDA, in this case).

The NMDA (N-methyl-D-aspartate) receptor is a major subclass of glutamate receptor (the most important excitatory neurotransmitter in the mammalian central nervous system). Importantly, activation of the NMDA receptor has been shown to be the central event which leads to excitotoxicity and neuronal death in many disease states, as well as a result of hypoxia and ischaemia following head trauma, stroke and following cardiac arrest.

It is known in the art that the NMDA receptor plays a major role in many higher cognitive functions, such as memory and learning, as well as in certain nociceptive pathways and in the perception of pain (Collingridge et al, The NMDA Receptor, Oxford University Press, 1994). In addition, certain properties of NMDA receptors suggest that they may be involved in the information-processing in the brain which underlies consciousness itself.

NMDA receptor antagonists in the context of the present invention are advantageous for a number of reasons, such as the following three specific reasons. Firstly, NMDA receptor antagonists confer profound analgesia, a highly desirable component of general anaesthesia and sedation. Secondly, NMDA receptor antagonists are neuroprotective under many clinically relevant circumstances (including ischemia, brain trauma, neuropathic pain states, and certain types of convulsions). Thirdly, NMDA receptor antagonists confer a valuable degree of amnesia.

The formulation may comprise one or more NMDA receptor antagonists.

Contrary to the prior art uses of NMDA receptor antagonists in general anaesthetic practice, we have surprisingly found that in the formulation of the present invention they are not severely hampered by their concomitant psychotomimetic effects and other undesirable side-effects. Prior art problems associated with this class of compounds included the production of involuntary movements, stimulation of the sympathetic nervous system, induction of neurotoxicity at high doses (which is pertinent since of NMDA receptor antagonists have low potencies as general anaesthetics), depression of the myocardium, proconvulsions in some epileptogenic paradigms e.g., "kindling" (Wlaz P et al, Eur. J. Neurosci. 1994; 6:1710–1719). Difficulties in developing antagonists that cross the blood-brain barrier had also limited their practical application.

In more detail, the NMDA receptor antagonists of the present invention may be competitive antagonists, such as 2-amino-5-phosphonopentanoate and 2-amino-7- phosphonoheptanoate, or derivatives or structural analogues thereof. The NMDA receptor antagonists may also be non-competitive antagonists, such as dizocilpine, ketamine, HA-966 [(+/−)-3-amino-1-hydroxy-2-pyrrolidone], or derivatives or structural analogues thereof.

Preferably, the NMDA receptor antagonist is xenon.

The advantage of using an inert, volatile gas such as xenon as a general anaesthetic is that the molecule can be rapidly eliminated via respiration.

In this respect, it has recently been discovered that xenon (which rapidly equilibrates with the brain) is an NMDA antagonist (Franks N P et al, Nature 1998; 396:324) making it a particularly attractive candidate in the context of the present invention.

Xenon is a chemically inert gas whose anaesthetic properties have been known for over 50 years (Lawrence J H et al, J. Physiol. 1946; 105:197–204). Since its first use in surgery (Cullen S C et al, Science 1951; 113:580–582), a number of research groups have shown it has an excellent pharmacological profile, including the absence of metabolic by-products, profound analgesia, rapid onset and recovery, and minimal effects on the cardiovascular system (Lachmann B et al, Lancet 1990; 335:1413–1415; Kennedy R R et al, Anaesth. Intens. Care 1992; 20:66–70; Luttropp H H et al, Acta Anaesthesiol. Scand. 1994; 38:121–125; Goto T et al, Anesthesiology 1997; 86:1273–1278; Marx T et al, Br. J. Anaesth. 1997; 78:326–327). Mechanistic studies on cultured hippocampal neurons have shown that 80% xenon, which will maintain surgical anaesthesia, reduces NMDA-activated currents by up to 60%. This powerful inhibition of the NMDA receptor explains some of the important features of the pharmacological profile and is likely to be instrumental in the anaesthetic and analgesic effects of this inert gas.

Up to now, a significant problem which has impeded the use of xenon as a new anaesthetic is its high cost and the need to use complex apparatus to minimise the volume used (low-flow systems), along with the need to scavenge the gas for reuse. A further problem was that the potency of xenon is relatively low. As a consequence, it had been suggested that volatile general anaesthetics may be solubilised in a lipid emulsion and administered intravenously (Eger R P et al, Can. J. Anaesth. 1995; 42:173–176). It is known in the art that local anaesthesia can be induced by intradermally injecting microdroplets of a general anaesthetic in a liquid form (Haynes D H, U.S. Pat. Nos. 4,725,442 and 44,622, 219). Typically these microdroplets are coated with a unimolecular phospholipid layer and remain stable in physiologically-compatible solutions. A similar approach is described in a recent patent application which proposes that xenon might be administered in this fashion (Georgieff M, European Patent Application No. 864329-A1).

It is to be noted that the prior art has neither disclosed nor suggested the use of an NMDA receptor antagonist with an alpha-2 adrenergic agonist in a formulation that has a broad applicability, especially for use as an anaesthetic, let alone the surprising properties associated therewith.

Another essential component of the formulation is an alpha-2 adrenergic agonist. The term "agonist" is used in its normal sense in the art, i.e., a chemical compound which functionally activates the receptor to which it binds.

Alpha-2 adrenergic receptors (adrenoceptors) are ubiquitously distributed in both the nervous system as well as in every other system in the body. Comprising three different receptor subtypes (termed A, B, and C), the alpha-2 adrenoceptors are activated by the non-selective endogenous adrenergic agonists adrenaline and noradrenaline which also activate six other adrenoceptor subtypes.

Up to now, anaesthetic interest has focussed on reductions in anaesthetic requirements as experimental and clinical studies have shown that alpha 2-agonists exert powerful analgesic (Guo T et al, Anesthesiology 1991; 75: 252–6) and anaesthetic effects. The hypnotic response is belived to be mediated by activation of alpha-2 adrenoceptors in the locus coeruleus, whereas the analgesia is induced by modulation of the nociceptive pathway at the level of the dorsal horn of the spinal cord and other sites not yet fully characterised (Guo T et al, ibid).

Thus, in the perioperative period alpha-2 adrenergic agonists are efficacious for decreasing anesthetic requirements for volatile (Aho M et al, Anesthesiology 1991; 74: 997–1002), opioid (Ghignone M et al, Anesthesiology 1986; 64: 36–42), and hypnotic agents (Aantaa R et al, Anesthesiology 1990; 73: 230–5). In addition, alpha-2 adrenergic agonists are also efficacious for anxyolysis (Uhde T W et al, Arch Gen Psychiatry 1989: 46: 170–7) and preoperative sedation (Flacke J W et al, Anesthesiology 1987; 67: 11–9) in the perioperative period.

More specifically, exogenous alpha-2 agonists such as dexmedetomidine induce loss of consciousness in experimental animals by activating the alpha 2A adrenoceptor subtype (Lakhlani P P et al, Proc. Nat. Acad. Sci. 1997; 94:9950–9955) in a discrete site in the brainstem (Correa-Sales C et al, Anesthesiol 1992c; 76: 948–52). When activated by its agonist, this same receptor subtype also reduces anxiety (anxiolysis) (Salonen M et al, Psychopharmacology 1992; 108:229–234) and activity in the sympathetic nervous system (sympatholysis). Alpha-2 agonists are also anticonvulsant in some types of epileptogenic paradigms (Halonen T et al, Brain Res. 1995; 6932:17–24) and are neuroprotective during ischaemic insults (Maier C et al, Anesthesiology 1993; 79:306–12). The alpha-2 agonist-induced hypnotic state can be reversed instantaneously with selective alpha-2 adrenergic antagonists (e.g, yohimbine). The alpha-2 agonists attenuate the excitement associated with emergence from the anaesthetic state produced by the volatile anaesthetic agents (Bruandet N et al, Anesth. Analg. 1998; 86:240–5).

Up to now, the use of alpha-2 adrenoceptor agonists in general anaesthetic practice has been hampered by their lack of anaesthetic potency and side-effect profile. Their lack of potency requires the use of very high doses which can activate non alpha 2A adrenoceptors resulting in peripheral vasoconstriction with an increase in blood pressure (Bloor B C et al, Anesthesiology 1992; 77:1134–1142) and a decrease in tissue perfusion. Furthermore, the alpha-2 agonists are also proconvulsant in some models of epilepsy ("pentylenetetrazol" [PTZ] seizures) (Mirski M A et al, Anesthesiology 1994; 81:1422–8).

It is well known in the art that both systemically and neuraxially administered alpha-2 agonists, such as clonidine and dexmedetomidine, alleviate pain in humans and in animal models. The alpha-2 agonists produce analgesia by a supraspinal (Guo T Z et al, ibid ) as well as by a local spinal action (Eisenach J et al, Anesthesiol. 1993: 277–87). Unlike local anesthetics, alpha-2 agonists do not change motor or sensory function, and unlike opiates they do not produce respiratory depression (Jarvis D A et al, Anesthesiology 1992; 76: 899–905) or induce drug-seeking behavior (i.e. addiction). As a result of these features, alpha-2 adrenergic agonists are attractive candidates for pain management and are effective for the reduction of post-operative pain (Bonnet F et al, Br J Anaesth 1989; 63: 465–9) and for pain relief during and after childbirth (Eisenach J C et al, Anesthesiology 1989; 71: 640–6; Filos K S et al, Anesthesiology 1992; 77: 267–74).

The potential of prolonged treatment with alpha-2 agonists for chronic pain states has undergone limited testing (Eisenach J C et al, Anesthesiology 1989; 71: 647–52) but appears to be very promising (Eisenach J C et al, Anesthesiology 1996; 85: 655–74). Clinical studies addressing the duration of the analgesic effects of epidural administration of alpha-2 agonists following prolonged administration have yet to be performed although alpha-2 agonists are now being advocated for prolonged periods of administration (Segal I S et al, Anesthesiology 1991; 74: 220–5) because of their potential benefit at each stage in the surgical patient's perioperative care. However, biologically important adaptations to the immediate effects of alpha-2 agonists may lead to a diminished drug effect over time; this is generally termed tolerance. While tolerance to the sedative actions of clonidine rapidly develops and is considered desirable in the treatment of hypertension it may mitigate the clinical utility of alpha-2 agonists for chronic pain relief and prolonged sedation in the intensive care setting (ICU) setting (Maze M, Redefining sedation, International Congress and Symposium, edited by Maze M, Morrison P. London, The Royal Society of Medicine Press, 1998, pp 3–11). Tolerance to the analgesic action of spinally administered alpha-2 agonists may be minimal as prolonged epidural administration of clonidine produced clinically useful analgesia for the treatment of chronic pain throughout the course of treatment (Eisenach J C et al, Anesthesiology 1989; 71: 640–6).

The formulation of the present invention may comprise one or more alpha-2 adrenergic agonists.

The alpha-2 agonist of the present invention may be clonidine (which may be sold as Catapress™ Boehringer Ingelheim; Duraclon™ Roxanne).

Clonidine, the prototypal alpha-2 adrenergic agonist, has been used as an antihypertensive agent since the early 1970's because of its sympatholytic properties. These sympatholytic, as well as anxiolytic, properties were exploited in the use of clonidine to facilitate drug and/or alcohol withdrawal (Gold M S et al, Psychiatr. Clin. North Am. 1993; 16:61–73). More recently it has been used as an analgesic and a sedative in the perioperative setting (Kamibayashi T et al, Current Opinion in Anaesthesiology 1996; 9:323–327) and for the management of psychological conditions such as attention-deficit hyperactivity disorder (van der Meere J et al, J. Child Psychol. Psychiatry 1999; 40:291–8). In particular, it has been shown that when added to local anaesthetic agents, clonidine increases the analgesic effects to a much greater extent than when a similar dose is administered systemically (Bernard J M et al, Can Anaesthesiol 1994; 42[2]:223–8). This effect is probably a consequence of the local clonidine concentration. Furthermore, extradural administration of clonidine is even more efficient than systemic administration, at least when high doses are injected.

In addition, or in the alternative, the alpha-2 agonist of the present invention may be detomidine, medetomidine, dexmedetomidine (which may be sold as Primadex, Abbott Labs.) brimonidine (which may be sold as Alphagan, Allergan), tizanidine, mivazerol (UCB-Pharma, Belgium), guanabenz (which may be sold as Wytensin™, Wyeth Ayerst), guanfacine (which may be sold as Tenex™, A H Robins), or a derivative or structural analogue thereof.

A preferred alpha-2 adrenergic agonist is dexmedetomidine.

It is to be noted that the prior art has neither disclosed nor suggested the use of an alpha-2 adrenergic agonist with an NMDA receptor antagonist in a formulation that has a broad applicability, especially for use as an anaesthetic, let alone the surprising properties associated therewith.

Thus, the present invention therefore relates to a formulation comprising an alpha-2 adrenergic agonist and an NMDA receptor antagonist. Here, the alpha-2 adrenergic agonists can prevent the posterior cingulate/retrosplenial (PC/RS) cortex neurotoxic side effects of NMDA antagonists (Jevtovic-Todorovic V et al, Brain Res. January 1998, 19;781[1–2]:202–11). In particular, the alpha-2 adrenergic agonist—such as clonidine and/or dexmedetomidine, which does not specifically relieve neuropathic pain—can potentiate the neuropathic pain-relieving action of an NMDA antagonist—such as MK-801, while also protecting against neurotoxicity and hyperactivity side effects of the NMDA antagonist. It is further known that oral clonidine premedication has been shown to attenuate the haemodynamic effects associated with ketamine anaesthetic induction in humans (Doak J G et al, Can. J. Anaesth. July; 1993 40[7]:612–8).

Preferably the NMDA receptor antagonist is not ketamine.

Preferably the alpha-2 adrenergic agonist is not xylazine.

More preferably, the formulation does not comprise the combination of ketamine and xylazine. In this respect, in veterinary anaesthetic practice the NMDA antagonist ketamine has been used in the presence of xylazine, a relatively weak alpha-2 agonist (Radde G R et al, Lab. Anim. 1996; 30:220–7). However, these drugs cannot be used in high enough doses to produce anaesthesia because of their side-effect profile which includes direct myocardial depression and hypertension. Like other TIVA regimens, the administration of these drugs requires kinetic mechanisms to terminate the effect and to facilitate emergence. Furthermore, extrapolation to facilitate general anaesthesia in human patients is complicated by involuntary movements and psychotomimetic effects.

The components of the formulation of the present invention may be administered consecutively, sequentially or simultaneously, or combinations thereof.

Preferably, the components of the formulation of the present invention are administered simultaneously, such as in a single formulation.

Thus, according to a preferred aspect of the present invention, general anaesthesia can be induced and maintained with a single formulation (monotherapy). This has the advantage that there is no requirement for the use of expensive equipment either for delivery or for ventilatory support. The favourable pharmacokinetic profile of the current invention allows both easy and rapid titratability for the desired effect as well as a smooth and rapid emergence from general anaesthesia. In particular, where general anaesthesia is used as a treatment (e.g., for withdrawal from alcohol and/or drug addiction; tetanus) the invention decreases the hyperactivity in the sympathetic nervous system as well as providing all the other features that are provided by a general anaesthetic.

According to the present invention, conscious sedation can be induced and maintained with monotherapy without requiring expensive equipment for either delivery or for monitoring of ventilation. Furthermore, chronic pain relief may be provided by monotherapy with no addictive potential and no ventilatory depression. In addition, neuroprotection can be provided with monotherapy, and does not result in the degree of cardiorespiratory depression which requires cardiovascular and respiratory resuscitation. The neuroprotective action is more efficacious as a result of the complementary action of the two components.

Preferably, the formulation of the present invention is in liquid form. For parenteral administration, the formulation may be used in the form of a sterile aqueous solution which may contain other substances, for example enough salts or monosaccharides to make the solution isotonic with blood.

More preferably, the formulation is in the form of a lipid emulsion. In the case a volatile anaesthetic such as xenon is used, the intravenous formulation typically contains a lipid emulsion (such as the commercially available Intralipid®10, Intralipid®20, Intrafat®, Lipofundin®S or Liposyn® emulsions, or one specially formulated to maximise solubility) to sufficiently increase the solubility of the gas or volatile anaesthetic to achieve the desired clinical effect. Further information on lipid emulsions of this sort may be found in G. Keinberger and H. Pamperl, Infusionstherapie, 108–117 (1983) 3.

The lipid phase of the present invention which dissolves or disperses the gas is typically formed from saturated and unsaturated long and medium chain fatty acid esters containing 8 to 30 carbon atoms. These lipids form liposomes in aqueous solution. Examples include fish oil, and plant oils such as soya bean oil, thistle oil or cottonseed oil. The lipid emulsions of the invention are typically oil-in-water emulsions wherein the proportion of fat in the emulsion is conventionally 5 to 30% by weight, and preferably 10 to 20% by weight. Oil-in-water emulsions of this sort are often prepared in the presence of an emulsifying agent such as a soya phosphatide.

The lipids which form the liposomes of the present invention may be natural or synthetic and include cholesterol, glycolipids, sphingomyelin, glucolipids, glycosphingolipids, phosphatidylcholine, phosphatidylethanolamine, phosphatidylserine, phosphatidyglycerol, phosphatidylinositol.

The lipid emulsions of the present invention may also comprise additional components. These may include antioxidants, additives which make the osmolarity of the aqueous phase surrounding the lipid phase isotonic with the blood, or polymers which modify the surface of the liposomes.

It has been established that appreciable amounts of xenon maybe added to a lipid emulsion. Even by the simplest means, at 20° C. and normal pressure, xenon can be dissolved or dispersed in concentrations of 0.2 to 10 ml or more per ml of emulsion. The concentration of dissolved gas is dependent on a number of factors, including temperature, pressure and the concentration of lipid.

The lipid emulsions of the present invention may be loaded with a gaseous or volatile anaesthetic. In general, a device is filled with the emulsion and anaesthetics as gases or vapours passed through sintered glass bubblers immersed in the emulsion. The emulsion is allowed to equilibrate with the anaesthetic gas or vapour at a chosen partial pressure. When stored in gas tight containers, these lipid emulsions show sufficient stability for the anaesthetic not to be released as a gas over conventional storage periods.

The lipid emulsions of the present invention may be loaded so that the xenon is at the saturation level. Alternatively, the xenon may be present in lower concentrations, provided, for example, that the administration of the emulsion (when in combination with the alpha-2 agonist) produces the desired pharmaceutical activity.

The present invention also relates to pharmaceutical compositions comprising the formulation of the invention and a pharmaceutically acceptable diluent, excipient or carrier. By way of example, in the pharmaceutical compositions of the present invention, the formulation of the present invention may be admixed with any suitable binder(s), lubricant(s), suspending agent(s), coating agent(s), solubilising agent(s) selected with regard to the intended route of administration and standard pharmaceutical practice.

In some instances, the formulation of the present invention may comprise further optional components, such as, for example, a nitric oxide (NO) synthase inhibitor.

In some instances, the presence of an NO synthase inhibitor is a preferred aspect. Here, it has been established that the sedative and analgesic effects of alpha-2 adrenergic agonists may diminish over time, a form of synaptic plasticity that is referred to as tolerance (Reid K et al, Pharmacol. Biochem. Behav. 1994;47:171–175).

Alterations in biologic responsiveness in the CNS, for example long-term potentiation (LTP), central sensitization ("wind-up") and tolerance, are referred to collectively as synaptic plasticity and their molecular mechanisms may be similar despite diverse provocative settings. Previous studies have revealed that both the NMDA receptor complex (Asztely F et al, Mol Neurobiol 1996; 12: 1–11) and nitric oxide synthase (NOS) (Meller S T et al, J. Neurosci. 1997; 17: 2645–51; Boxall A R et al, Eur J Neurosci 1996; 8: 2209–12) are pivotal for some forms of synaptic plasticity. Studies have also shown that less exposure to alpha-2 agonists is required to achieve hypnotic tolerance than for analgesic tolerance (Hayashi Y et al, Anesthesiology 1995; 82: 954–62) suggesting that these two forms of tolerance may have different biological substrates.

In particular, studies have revealed that the induction of tolerance to the hypnotic effect of dexmedetomidine is blocked by co-administration of either dizolcipine or the NOS inhibitor $NO_2$-Arginine. However, after tolerance has developed, acute administration of dizolcipine or $NO_2$-Arginine does not prevent the expression of tolerance, i.e., neither NMDA receptors nor NOS inhibitors can affect the expression of hypnotic and analgesic tolerance, suggesting that there are multiple mechanisms by which behavioral tolerance to alpha-2 agonists may be induced and maintained.

Further studies using the pharmacologic probes MK-801, ketamine and $NO_2$-arginine also strongly suggest that tolerance has at least two distinct phases (induction and expression) as is seen in other forms of synaptic plasticity (e.g. LTP), and that the components of the signaling pathway follow in an orderly temporal sequence.

Previous work has elucidated key sites for the hypnotic and analgesic action of alpha-2 agonists. The locus coeruleus (LC) appears to be a pivotal site for producing alpha-2 agonist-induced hypnosis (Correa-Sales C et al, ibid). However the analgesic effects of alpha-2 agonists are mediated both spinally and supraspinally. The analgesic action of dexmedetomidine injected directly into the LC results from activation of alpha-2 adrenoceptors in the spinal cord, since this analgesia can be blocked by intrathecal injection of the alpha-2 antagonist atipamezole and also by intrathecal administration of pertussis toxin (Guo T Z et al, ibid) which ribosylates, and thereby inactivates, defined species of G proteins. Intrathecal administration of alpha-2 agonists such as clonidine (Post C et al, J. Anesth Analg 1987; 66: 317–24; Ossipov M H et al, J Pharmacol Exp Ther 1990; 255: 1107–16) or dexmedetomidine (Guo T Z et al, ibid; Fisher B et al, Eur J Pharmacol 1991; 192: 221–5) also produce analgesia. These data point to spinal alpha-2 adrenoceptors as a "final common pathway" in antinociception.

Initially, the alpha-2 adrenoceptor system was thought to have many similarities with the opiate receptor system based on similarities in their physiologic actions in the LC (Aghajanian G K et al, Neuropharmacol 1987; 26: 793–9; Williams J T et al, J Neurosci 1988; 8: 4299–306) and spinal cord (Yoshimura M et al, Nature 1983; 305: 529–30; North R A et al, J Physiol (Lond) 1984; 349: 43–55), and in their actions on nociceptive processing in the spinal cord (Kendig J J et al, Eur J Pharmacol 1991; 192: 293–300; Feng J et al, Pain 1996; 66: 343–9). However in contrast to alpha-2 agonist analgesic tolerance, development of opiate analgesic tolerance is sensitive to NMDA receptor antagonists (Marek P et al, Brain Res 1991; 558: 163–5; Ben-Eliyahu S et al, Brain Res 1992; 575: 304–8; Tiseo P J et al, J Pharmacol Exp Ther 1993; 264: 1090–6; Trujillo K A et al, Science 1991; 251: 85–7) and NOS inhibitors (Kumar S et al, Gen Pharmacol 1997; 29: 223–7; Highfield D A et al, Synapse 1998; 29: 233–9; Bhargava H N, Pharmacology 1994; 48: 234–41). The lack of effect of NMDA and NOS inhibitors in alpha-2 analgesic tolerance therefore strongly suggests that the mechanisms underlying alpha-2 and opiate tolerance are different.

The pharmaceutical composition of the present invention may also comprise other active ingredients. Examples of such other ingredients include L-type calcium channel blockers, N-type calcium channel blockers, substance P antagonists, sodium channel blockers, purinergic receptor blockers, or combinations thereof Preferably, the formulation (or pharmaceutical composition thereof) of the present invention may be delivered intravenously (either by bolus administration or infusion), neuraxially (either subdural or subarachnoid) or transdermally.

The formulation of the present invention may also be administered in the form of an ointment or cream (lipid emulsion or liposomes) applied transdermally. For example, the formulation of the present invention may be incorporated into a cream consisting of an aqueous emulsion of polyethylene glycols or liquid paraffin. Alternatively, the formulation of the present invention may be incorporated, at a concentration of between 1 and 10% by weight, into an ointment consisting of a white wax or white soft paraffin base together with such stabilisers and preservatives as may be required. These ointments or creams are suitable for the local alleviation of pain and may be applied directly to damaged tissue, often with the aid of an optionally air-tight wound closure.

The concentrations employed in the formulation may be the minimum concentrations required to achieve the desired clinical effect. Typically, the concentrations of both drugs (NMDA receptor antagonists and alpha-2 adrenergic agonists) will be lower, and in some cases substantially lower, than the concentrations required if each of the drugs were to be used separately. It is usual for a physician to determine the actual dosage that will be most suitable for an individual patient, and this dose will vary with the age, weight and response of the particular patient. There can, of course, be individual instances where higher or lower dosage ranges are merited, and such are within the scope of this invention.

The formulation of the present invention may be for human administration or animal administration.

Thus, the formulation of the present invention may also be used as an animal medicament. In this regard, the invention further relates to a veterinary composition comprising the formulation of the present invention and a veterinarily acceptable diluent, excipient or carrier.

For veterinary use, the formulation of the present invention, or a veterinarily acceptable formulation thereof, is typically administered in accordance with normal veterinary practice and the veterinary surgeon will determine the dosing regimen and route of administration which will be most appropriate for a particular animal.

In a broad aspect, the present invention provides a pharmaceutical composition comprising a combination of an NMDA antagonist and an alpha-2 adrenergic agonist.

Here, the pharmaceutical composition may be for any one or more of:

a) to diminish the harmful effects of stroke (such as stroke from reduced blood supply to the brain);

b) to provide neuroprotection after trauma;

c) to relieve pain, such as chronic pain;

d) to produce sedation and/or general anaesthesia;

e) to ameliorate withdrawal symptoms in addicted patients;

f) to reduce anxiety—such as panic syndrome disorders;

g) to prevent convulsions and sympathetic hyperactivity in patients with tetanus.

Thus, the present invention also encompasses the use of a formulation of the present invention in the manufacture of a medicament:

a) to diminish the harmful effects of stroke (such as stroke from reduced blood supply to the brain); and/or b) to provide neuroprotection after trauma; and/or c) to relieve pain, such as chronic pain; and/or d) to produce sedation and/or general anaesthesia; and/or e) to ameliorate withdrawal symptoms in addicted patients; and/or f) to reduce anxiety—such as panic syndrome disorders; and/or g) to prevent convulsions and sympathetic hyperactivity in patients with tetanus.

In a preferred embodiment, the present invention provides an improved formulation for use in anaesthesia in which an NMDA receptor antagonist and an alpha-2 adrenergic agonist are combined, preferably in a form suitable for intravenous administration.

The present invention also relates to the use of the anaesthetic (or pharmaceutical composition thereof) of the invention for the induction and/or maintenance of anaesthesia.

The formulation of the present invention may also be used for general anaesthesia to facilitate surgery, drug/alcohol withdrawal, treatment of tetanus, and other diagnostic/therapeutic interventions. In particular, the present invention may be used to maintain general anaesthesia for extended periods (24–48 h) in addicted patients during which drug and/or alcohol withdrawal is provoked. The invention can be used to maintain general anaesthesia for prolonged periods (days to weeks) in the management of patients with tetanus. The anaesthetic of the invention may also be used to render patients sedated and pain-free to facilitate surgical and other therapeutic interventions (including endotracheal mechanical ventilation, wound dressing change in patients with burns) or diagnostic procedures (including endoscopy and imaging techniques) for which loss of consciousness is not required (conscious sedation).

Furthermore, the formulation of the invention may be used to prevent and/or treat the consequences of injury (including ischaemic and traumatic) to the nervous system. It is known in the art that a combination of intravenous agents have been employed to antagonise the toxic effects of the mediating excitatory amino acids, including glutamate.

However, while the blockade of NMDA receptors has been shown to be efficacious in animal models, clinical trials have revealed that significant neurotoxicity is associated with this class of compounds. This neurotoxicity may be preventable through the neuroprotective action of the alpha-2 agonists used in the current invention.

The formulation of the invention may also be used to treat chronic pain states. It is known in the art that agents of many drug classes (including opioids and non-opioids) have been used by several different routes either alone or in combination. However, synergistic interactions between the NMDA antagonist and the alpha-2 agonist of the present invention may limit the dose and maintain prolonged efficacy by preventing the onset of tolerance.

The formulation of the present invention may also be used in the treatment of optic nerve damage caused by acute glaucoma. The lowering of the intra-ocular pressure by the alpha-2 agonist, combined with the neuronal injury protection effect of the NMDA antagonist may lead to a treatment which is highly efficacious.

The combination of a potent alpha-2 agonist and a rapidly-eliminated NMDA antagonist (such as xenon) may be advantageous for several other reasons. Firstly, the convergence of two disparate transmembrane signalling pathways (alpha-2 adrenoceptors and NMDA receptors) on the same or different neurones, onto the molecular mechanism for anaesthesia may result in multiplicativity of effectiveness. For example, alpha-2 agonists have a dual effect by both reducing membrane excitability directly via the opening of potassium channels and the closing of calcium channels (Nacif-Coelho C et al, Anesthesiology 1994; 81:1527–1534), and also as a consequence of the adrenoceptor-induced hyperpolarisation, by making it less probable that glutamate release will trigger an action potential by NMDA-receptor activation. Similarly, the inhibition of NMDA receptors by NMDA antagonists will reduce excitability both directly by inhibiting depolarisation via NMDA receptor channels, and also, because the blocking of basal activation of NMDA receptors will cause a reduction in membrane conductance, the hyperpolarisation due to alpha-2 agonist action will be enhanced. In addition, release of glutamate at NMDA synapses may be inhibited by presynaptic effects of alpha-2 agonists, again conferring synergy. Finally, these two classes of agents may exert a synergistic action on muscle relaxation by inhibiting the release (alpha-2 agonist) and the modulatory action of glutamate (NMDA antagonist) at the neuromuscular junction (El Tamer A et al, J. Neurochem. 1996; 67:636–44; Koyuncuoglu H et al, Pharmacol. Res. 1998; 37:485–91).

The adverse effects of each (NMDA antagonist and alpha-2 agonist) may be antagonised by the other. Thus the anti- and pro-convulsant actions of one drug may be offset by the other. The vasoconstrictive properties of alpha-2 agonists are transduced via the alpha-2B adrenergic receptor subtype (Link R E et al, Science 1996; 273:803–5) which may have a diametrically opposite signalling pathway to that present in the transduction of the beneficial anaesthetic actions which are mediated by the alpha-2A adrenoceptor subtype. Thus the signalling via the alpha-2B adrenoceptor may be interrupted by the NMDA antagonists, thereby relaxing the tension developed in the vascular smooth muscle cells by activation of subtype non-selective alpha-2 agonists (Kaye A D et al, Anesth. Analg. 1998; 87:956–62). The development of tolerance to the anaesthetic actions of the alpha-2 agonist may require the participation of NMDA receptors, which if concurrently blocked, may interrupt this biologic process. Since xenon is kinetically inert it should not adversely affect the kinetic profile of alpha-2 agonists and thus emergence from anaesthesia could be predictable, smooth and rapid.

The invention will now be described only by way of example and with reference to the accompanying figures wherein.

In more detail, in FIG. 1A, rats were given dexmedetomidine (5 μg/hg/hr) for 7 days then injected with challenge doses of dexmedetomidine and the duration of loss of righting reflex recorded. All values are mean±standard error of 4–11 rats. In FIG. 1B, rats were given dexmedetomidine (10 μg/hg/hr) for 14 days then injected with challenge doses of dexmedetomidine 30 min prior to analgesia testing. All values are mean±standard error of 5–14 rats.

Figure 2:
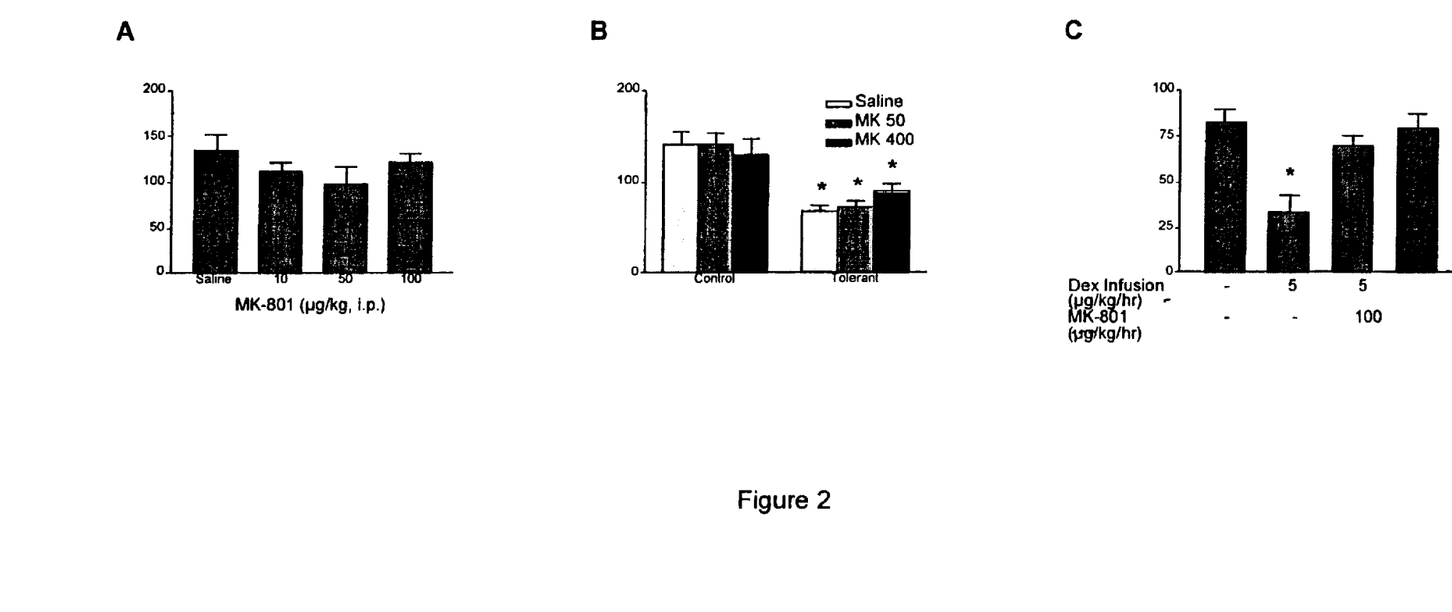
FIG. 2 shows the results of MK-801 administration on the sleep time induced by dexmedetomidine.

In more detail. FIG. 2A shows the effect of acute administration of MK-801 (10–200 μg/kg) on the sleep time induced by acute administration of dexmedetomidine (100 μg/kg, i.p.). $*p<0.05$ different from saline, n=6. FIG. 2B illustrates that acute administration of MK-801 does not block dexmedetomidine-induced tolerance to the hypnotic effect of dexmedetomidine. $*p<0.05$ different from control saline, n=6–7. FIG. 2C illustrates that co-administration of MK-801 (100 and 400 μg/kg/hr) blocks tolerance to the hypnotic effects of a challenge dose of dexmedetomidine (100 μg/kg, i.p.). $*p<0.05$ different from control, N=6–8. All values are mean±standard error of 7–8 rats.

Figure 3:
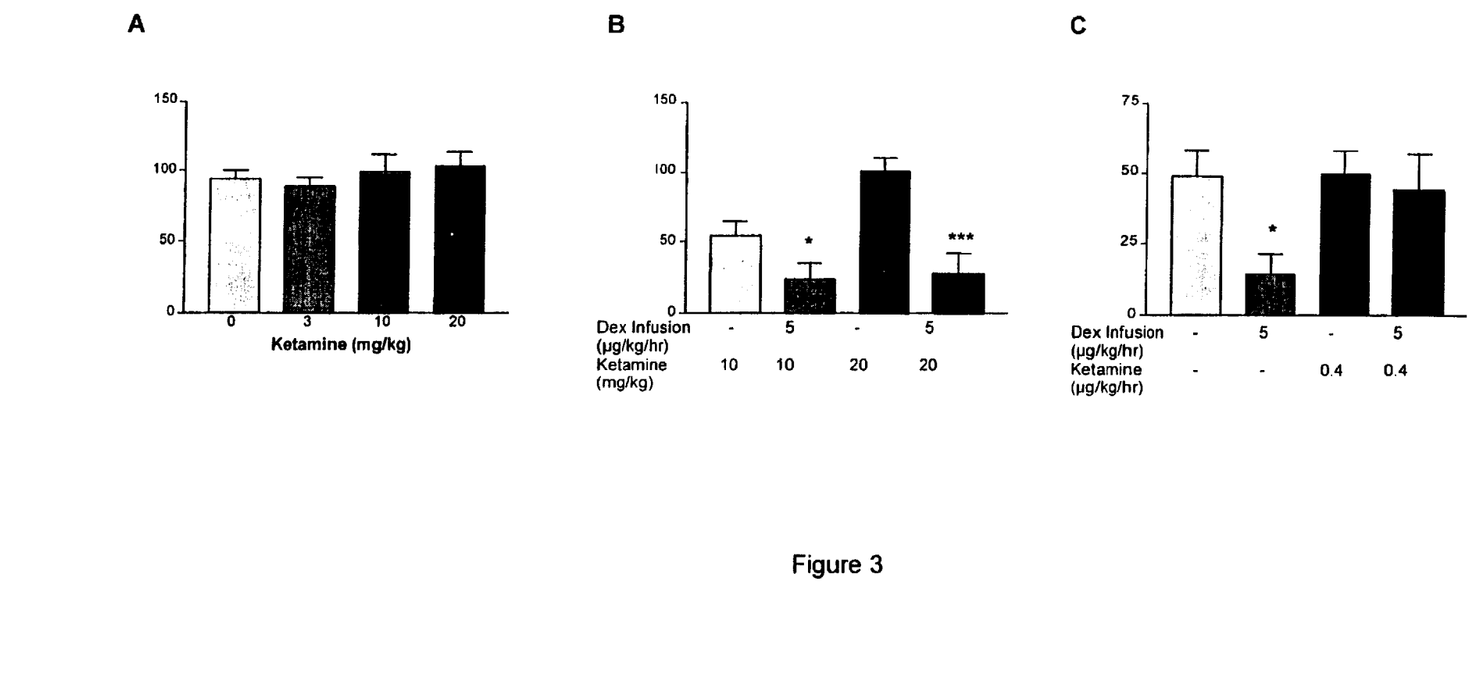
FIG. 3 shows the results of ketamine administration on the sleep time induced by dexmedetomidine.

In more detail, FIG. 3A, shows that acute administration of ketamine has no effect on the sleep time induced by dexmedetomidine (150 μg/kg i.p.). FIG. 3B shows that acute administration of ketamine (10 and 20 mg/kg) does not block dexmedetomidine-induced tolerance to the hypnotic effect of dexmedetomidine. $*=p<0.05$ different from 10 mg/kg ketamine to sham treated animals, $***<0.001$ different from 20 mg/kg ketamine to sham treated animals. FIG. 3C shows that co-administration of ketamine (400 μg/kg/hr) reverses tolerance to the hypnotic effects of a challenge dose of dexmedetomidine (150 μg/kg, i.p) without having an effect on dexmedetomidine sedation when administered alone. $p<0.05$ significantly different from sham N=6–8. All values are mean±standard error of 7–8 rats.

Figure 4:
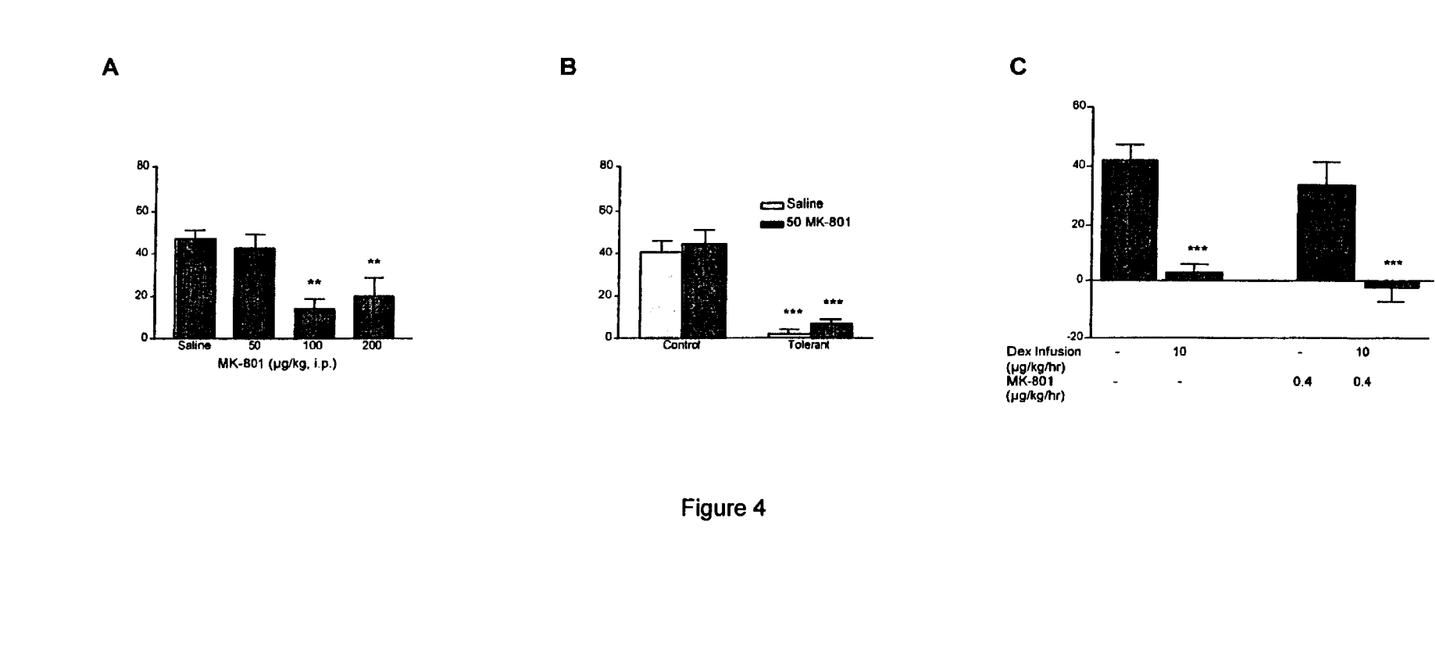
FIG. 4 shows the results of MK-801 administration on the analgesic effects induced by dexmedetomidine.

In more detail, FIG. 4A shows the effect of acute administration of MK-801 on the analgesic action of dexmedetomidine in naive rats. MK-801 was administered 15 min before the administration of 50 μg/kg dexmedetomidine and the tail flick test was performed 40 min later. $=p<0.01$, n=6–7. FIG. 4B shows that acute administration of MK-801 does not prevent the development of tolerance. In rats rendered tolerant by implantation of minipumps that delivered dexmedetomidine (10 μg/kg/hr) for 14 days, MK-801 (50 μg/kg) does not prevent the expression of tolerance. This dose of MK-801 was chosen because it has no effect on dexmedetomidine-induced sleep time. $*=p<0.001$, n=6–7. FIG. 4C illustrates that co-administration of MK-801 (0.4

μg/kg/hr), with dexmedetomidine (10 μg/kg/hr) for 14 days does not prevent the development of tolerance. This dose of MK-801 alone does not affect dexmedetomidine's analgesic action, ***=p<0.001 significantly different from control. All values are mean±standard error of 7–8 rats.

Figure 5:
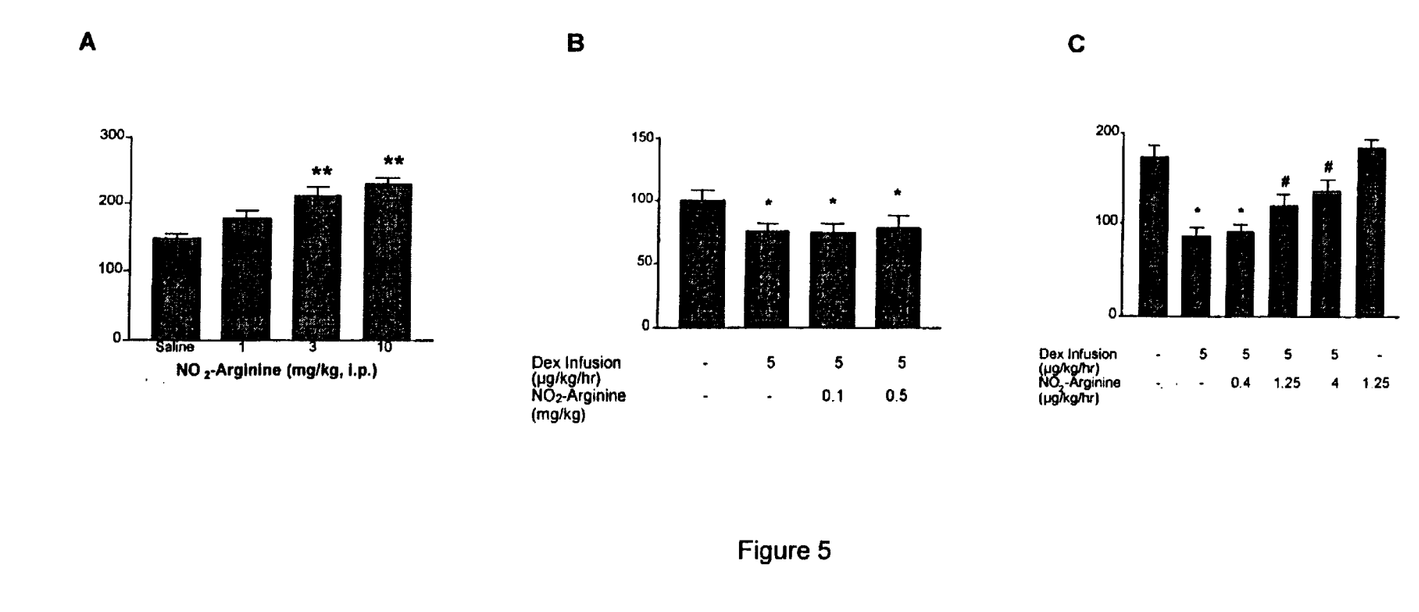
FIG. 5 shows the results of $NO_2$-Arginine administration on the sleep time induced by dexmedetomidine.

In more detail, FIG. 5A shows that a dose of $NO_2$-arginine dependently increases the dexmedetomidine-induced sleep time of drug naive rats. $NO_2$-arginine was administered 15 min prior to the administration of dexmedetomidine (100 μg/kg i.p.). *=p<0.01 n=8. FIG. 5B shows that the acute administration of a dose of $NO_2$-arginine that does not affect dexmedetomidine-induced sleep time does not reverse the tolerance to the hypnotic effect of dexmedetomidine (100 μg/kg). *=p<0.05 different from control, n=8. FIG. 5C shows that the concurrent administration of $NO_2$-arginine 0.4–4 μg/kg/hr with dexmedetomidine (5 μg/kg/hr) for 7 days dose-dependently blocks the development of tolerance to the hypnotic effect of dexmedetomidine *=p<0.05 different from control; #=p<0.05 different from both control and dexmedetomidine tolerant group, n=7–8. Treatment with just $NO_2$-arginine 1.25 μg/kg/hr (last column) does not affect the dexmedetomidine-induced sleep time. N=8. All values are mean±standard error of 7–8 rats.

Figure 6:
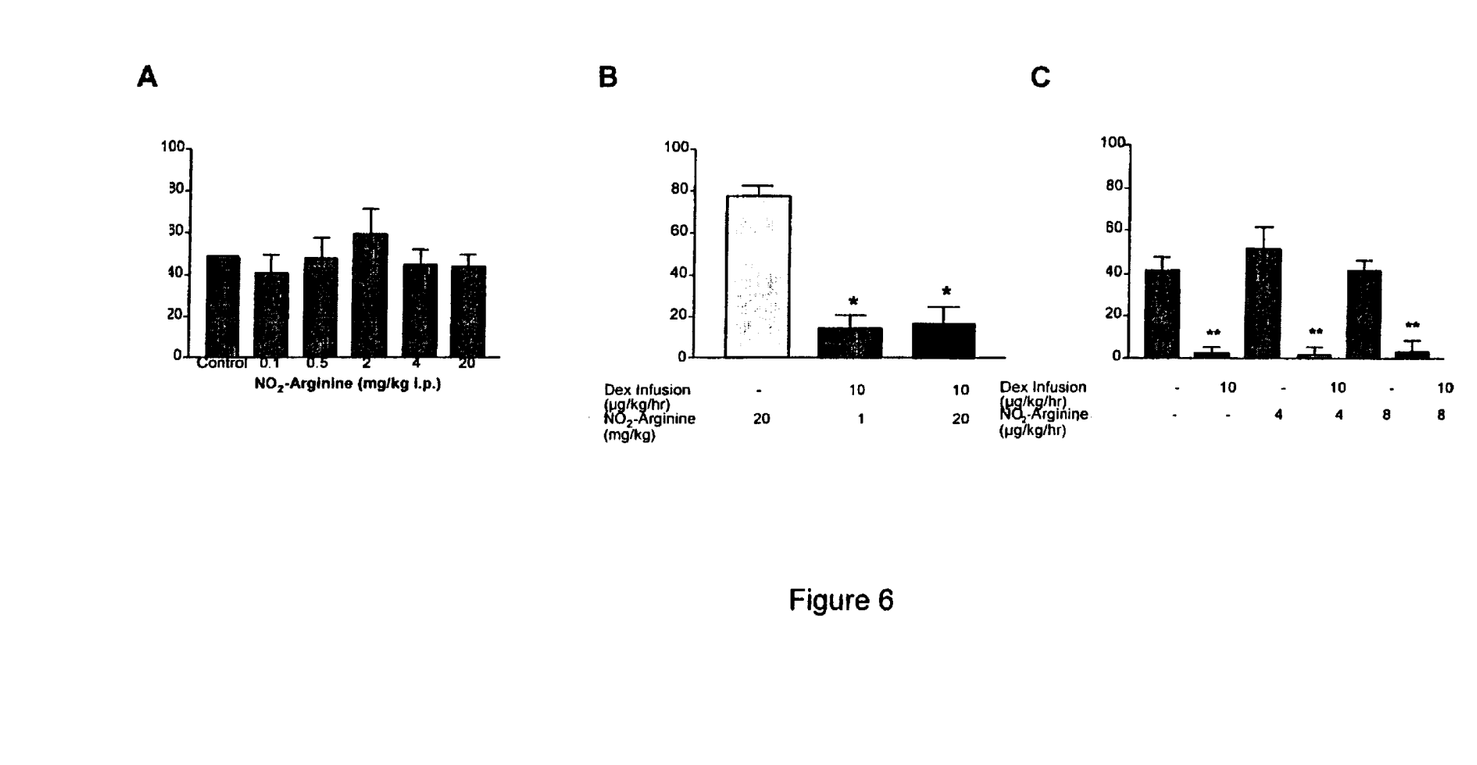
FIG. 6 shows the results of $NO_2$-Arginine administration on the analgesic effects induced by dexmedetomidine.

In more detail, FIG. 6A shows that acute administration of $NO_2$-arginine has no effect on the analgesic action of dexmedetomidine in naïve rats. $NO_2$-arginine was administered intraperitoneally 15 min prior to administration of dexmedetomidine (50 μg/kg i.p.) and the tail flick test was administered 40 min later. All values are mean±standard error of 6 rats. FIG. 6B shows that $NO_2$-arginine (1 and 20 mg/kg i.p.) does not reverse dexmedetomidine tolerance to the analgesic action of dexmedetomidine (100 μg/kg i.p.) in dexmedetomidine tolerant rats. *=p<0.05 significantly different from control. N=7–8. FIG. 6C shows that co-administration of a dose of $NO_2$-arginine (4 μg/kg/hr) that effectively antagonizes hypnotic tolerance (see FIG. 5C), has no effect on analgesic tolerance produced by dexmedetomidine (10 μg/kg/hr for 14 days). Increasing the dose of $NO_2$-arginine to 8 μg/kg/hr was also ineffective. All values are mean±standard error of 7–8 rats. *=p<0.05**=p<0.01 significantly different from control.

EXAMPLE

Example of the Formulation

A typical formulation of the present invention comprises from 5–30 mM of xenon, and from 7–70 μM of dexmedetomidine in a 10–20% Intralipid™ emulsion. In each of the following examples, the xenon gas is dissolved in the lipid emulsion.

Example 1

In order to induce general anaesthesia, an adult patient is injected intravenously over 2 minutes with the formulation containing 5–20 mls of xenon gas and 15–300 micrograms of dexmedetomidine. The induction of anaesthesia may facilitate [a] surgery, [b] withdrawal from drug and/or alcohol addiction, [c] management of tetanus.

Example 2

In order to maintain general anaesthesia (in order to facilitate [a] surgery, [b] withdrawal from drug and/or [c] alcohol addiction, management of tetanus), an adult patient receives an intravenous infusion of the formulation which is set to deliver 10–50 mls of xenon gas and 10–150 micrograms of dexmedetomidine each hour.

Example 3

To provide conscious sedation, an adult patient is injected intravenously with the formulation containing 1–10 mls of xenon gas and 5–100 micrograms of dexmedetomidine over 10 minutes and receives an intravenous infusion of the formulation which is set to deliver 5–20 mls of xenon gas and 2–30 micrograms of dexmedetomidine each hour. Conscious sedation may facilitate diagnostic, or therapeutic (surgical and non-surgical) procedures.

Example 4

To protect against ongoing neural damage from trauma or ischaemia, an adult patient is injected intravenously with the formulation containing 5–20 mls of xenon gas and 15–300 micrograms of dexmedetomidine over 10 minutes. This is then followed by a continuous infusion with the formulation set to deliver 10–50 mls of xenon gas and 10–150 micrograms of dexmedetomidine each hour.

Example 5

In the treatment of chronic pain, an adult patient is injected epidurally with the formulation containing 1–10 mls of xenon gas and 5–60 micrograms of dexmedetomidine over 10 minutes. This is followed by a continuous infusion with the formulation set to deliver 2–20 mls of xenon gas and 1–20 micrograms of dexmedetomidine each hour.

Example 6

In an alternative treatment for chronic pain in an adult patient, the formulation is applied transdermally and is set to deliver 5–20 mls of xenon gas and 2–30 micrograms of dexmedetomidine each hour.

The Effect of NMDA Receptor Inhibitors on Alpha-2 Agonist Tolerance

The experimental protocol was approved by the Animal Care and Use Committee of the Veterans Affairs Palo Alto Health Care System. Male Sprague-Dawley rats, (B&K, Fremont, Calif.) weighing 250–350 g were used. The rats were stratified to match the distribution of the weights in the groups as closely as possible. All tests were performed between 10 a.m. and 4 p.m. The number of animals for each experiment is listed in the legends.

Development of Tolerance

Rats were made tolerant to the anesthetic action of an alpha-2 agonist, dexmedetomidine, as described by Reid K et al (ibid). Briefly, rats were administered dexmedetomidine chronically using Alzet® osmotic minipumps (Model 2002 or 1007D, Alza, Palo Alto Calif.), which discharge their contents at a mean pumping rate of 0.48±0.02 μl/h. The pumps were inserted subcutaneously during isoflurane anesthesia in the dorsal thoracic region and loaded to deliver 5 μg/kg/h for 7 days to induce hypnotic tolerance and 10 μg/kg/h for 14 days to induce analgesic tolerance. These dosing schedules were previously found to be optimal to generate a tolerant hypnotic or analgesic state (Hayashi Y et al, ibid). When MK-801 or Nω-nitro-L-arginine ($NO_2$-arginine) was co-administered with dexmedetomidine the MK-801 was included in the same pump. Previous studies (Hayashi Y et al, ibid) have reported that the behavioural responses measured in sham surgery animals did not differ from rats implanted with pumps containing saline, therefore the former were used. For the MK-801 and Nω-nitro-L-arginine (NO2-arginine) hypnotic experiments the pumps were removed one day prior to behavioral testing. In all other experiments the pumps were not removed prior to testing.

Loss of Righting Reflex

Hypnotic response to dexmedetomidine, was defined by the loss of the rat's righting reflex (LORR), and its duration was measured in minutes and referred to as sleep-time. The duration of the LORR was assessed as the time from the rat's inability to right itself when placed on its back until the time that it spontaneously reverted, completely, to the prone position. The hypnotic response test was performed between 10 a.m. and 6 p.m. as described in Reid et al, 1994.

Nociceptive Testing Procedures

Nociceptive response was assessed by the tail flick response to a noxious thermal stimulus 40 minutes after the administration of the dexmedetomidine challenge dose. A high intensity light beam focused on the tail and the time for the rat to move its tail out of the light was recorded as tail flick latency. This method has been described previously in the literature (Guo T Z et al, ibid). The latencies from three sites on the tail were averaged. A cut-off time of 10 sec was predetermined to prevent tissue damage. Baseline measurements consist of a set of three tail flick determinations at 2 min intervals. Baseline tail flick latencies ranged between 3–4 sec.

Drug Preparation

The NOS inhibitor Nω-nitro-L-arginine ($NO_2$-arginine) (Sigma) and the NMDA antagonists MK-801 (RBI) and ketamine (Sigma) were diluted in normal saline and acutely administered intraperitoneally or administered chronically by means of Alzet® osmotic minipumps (Model 2002 or 1007D, Alza, Palo Alto Calif.). These compounds were co-administered with dexmedetomidine by including both drugs in one pump.

Statistical Analysis

LORR and tail flick data was analyzed using the analysis of variance (ANOVA) followed by post hoc Bonferroni tests or Dunnett's multiple comparison test or t-test where appropriate.

Figure 1:
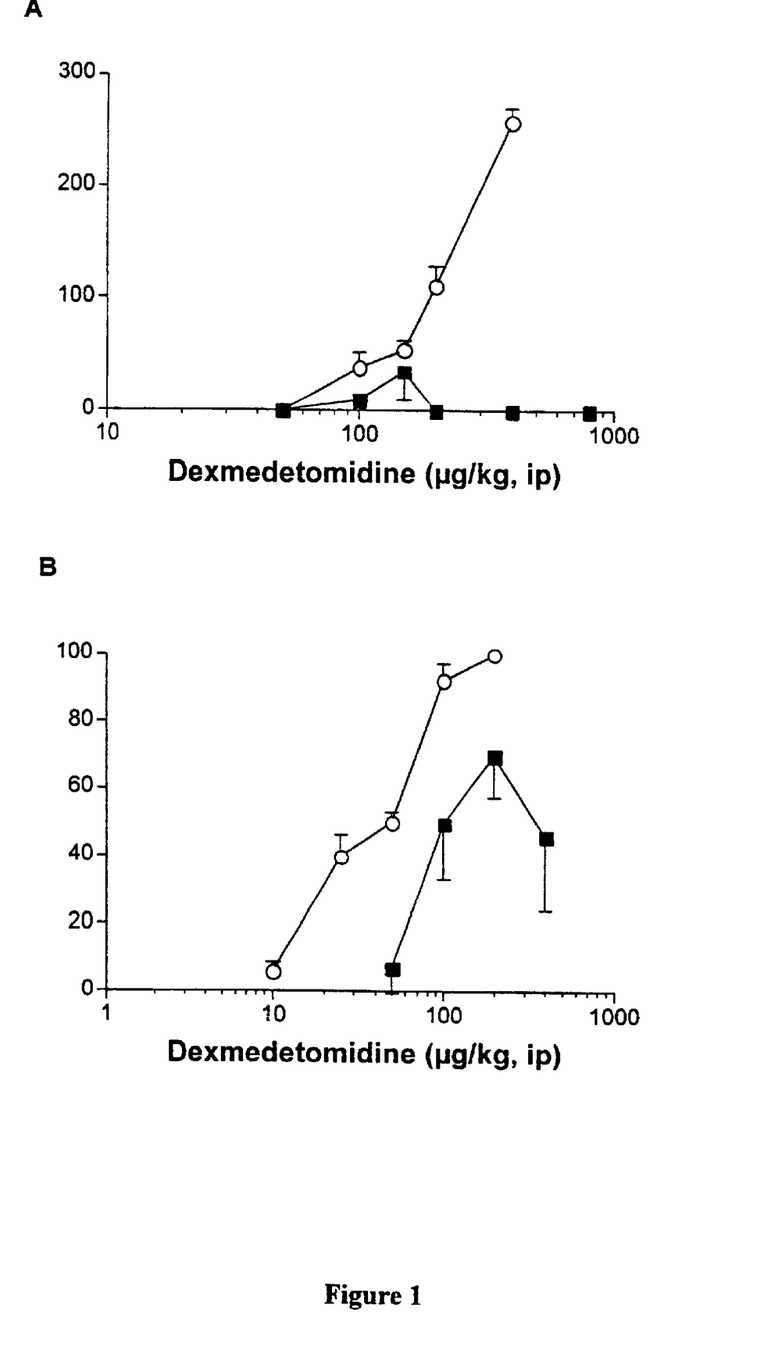
FIG. 1 shows the dose response relationship for the hypnotic and analgesic actions of dexmedetomidine in rats treated with sham surgery or chronically with dexmedetomidine.

Dose-response Relationship for Dexmedetomidine in Sham and Chronically Treated Animals The dose response relationships for the hypnotic and analgesic effect of dexmedetomidine are shown in FIG. 1. The hypnotic effect of dexmedetomidine dose dependently increased in sham treated animals but was almost completely absent in rats chronically treated for 7 days even when large doses were given (FIG. 1A). A biphasic dose response curve for this action of dexmedetomidine with a maximal efficacy around 300 μg/kg has been previously demonstrated and has been shown to be due to a stimulatory action of dexmedetomidine mediated by activation of $\alpha_1$ receptors (Guo T Z et al, ibid).

Chronic exposure to dexmedetomidine for 14 days shifted the analgesic dose response curve for dexmedetomidine about 2 fold and reduced the maximal effect (FIG. 1B).

Prevention of the Induction of Tolerance to the Hypnotic Effects of Dexmedetomidine with the NMDA Receptor Antagonists MK-801 and Ketamine Acute administration of MK-801 to naive animals did not affect sleep time (FIG. 2A). Once tolerance had developed acute administration of MK-801 did not affect the expression of tolerance (FIG. 2B). However co-administration of MK-801 with dexmedetomidine was able to prevent the development of tolerance (FIG. 2C). In this experiment the osmotic pumps were removed 1 day prior to behavioral testing.

Ketamine had a similar profile in that when acutely administered it did not affect the sleep time caused by acute injection of dexmedetomidine (FIG. 3A). Acute administration of 10 or 20 mg/kg ketamine could not reverse tolerance that was previously established (FIG. 3B) but ketamine did reverse tolerance to the sedative actions of dexmedetomidine when administered concurrently (FIG. 3C). This same dose of ketamine had no effect by itself. In this experiment the Alzet pumps were left in place for the behavioral testing.

Lack of Prevention of the Induction of Tolerance to the Analgesic Effects of Dexmedetomidine with MK-801

Acute administration of MK-801 15 min prior to the challenge dose of dexmedetomidine suppressed its analgesic action at the two highest doses (FIG. 4A). To determine whether MK-801 could affect the expression of tolerance, it was acutely administered to control and tolerant animals. A low dose of MK-801, that alone did not have any affect on dexmedetomidine-induced analgesia, did not reverse the expression of tolerance (FIG. 4B). A higher dose of MK-801 (400 μg/kg) that antagonized the analgesic action of dexmedetomidine in control animals was also unable to reverse tolerance. Co-administration of a dose of MK-801 that prevented the development of tolerance to the hypnotic effect of dexmedetomidine and was the maximum dose tolerated by the rat had no effect on the development of analgesic tolerance (FIG. 4C). This dose of MK-801 had no effect on tail flick latency when administered alone.

Prevention of the Induction of Tolerance to the Hypnotic Effects of Dexmedetomidine with a NO Synthase Inhibitor When administered to naive animals $NO_2$-arginine increased sleep time only at high doses (FIG. 5A). Once tolerance had been developed by a 7-day administration of dexmedetomidine, acute administration of low doses of $NO_2$-arginine, that did not affect sleep time in naive animals, did not reverse its expression (FIG. 5B). When $NO_2$-arginine was co-administered with dexmedetomidine, the induction of tolerance to the hypnotic effects of dexmedetomidine was attenuated (FIG. 5C). Treatment with just $NO_2$-arginine 1.25 μg/kg/hr (last column) did not affect the dexmedetomidine sleep time.

Lack of Prevention of the Induction of Tolerance to the Analgesic Effects of Dexmedetomidine with $NO_2$-arginine Acute administration of $NO_2$-arginine did not affect the analgesic action of dexmedetomidine (50 μg/kg i.p.) (FIG. 6A). To determine if $NO_2$-arginine could affect the expression of tolerance it was acutely administered to control and tolerant animals. $NO_2$-arginine (1 and 20 mg/kg i.p.) did not reverse the expression of tolerance (FIG. 6B). Co-administration of a dose of $NO_2$-arginine (4 μg/kg/hr), a dose that prevented the development of tolerance to the hypnotic effect of dexmedetomidine, had no effect on dexmedetomidine-induced analgesia in control animals and had no effect on analgesic tolerance (FIG. 6C). This dose of $NO_2$-arginine had no effect on tail flick latency when administered alone (data not shown). Increasing the dose of $NO_2$-arginine further to 8 μg/kg/hr was also ineffective at reversing tolerance.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in the relevant fields are intended to be within the scope of the following claims.

What is claimed is:

1. A synergistic pharmaceutical composition in liquid form, consisting essentially of an NMDA antagonist and an alpha-2 adrenergic agonist wherein the said NMDA antagonist is xenon.

2. A composition according to claim 1 wherein the alpha-2 adrenergic agonist is dexmedetomidine.

3. A composition according to claim 1 wherein the composition is in the form of a lipid emulsion.

4. A method of inducing anaesthesia in a subject in need of same, the method comprising administering to said subject a formulation as defined in claim 1 in an amount sufficient to induce synergistic anaesthesia.

5. A method according to claim 4 wherein the alpha-2 adrenergic agonist is dexmedetomidine.

6. A method according to claim 4 wherein the formulation is delivered intravenously, neuraxially or transdermally.

* * * * *